(12) United States Patent
Messal et al.

(10) Patent No.: US 8,277,479 B2
(45) Date of Patent: Oct. 2, 2012

(54) SELF-OPENING FILTER WITH WIRE ACTUATION

(75) Inventors: Todd P. Messal, Plymouth, MN (US); Timothy M. Stivland, Plymouth, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 885 days.

(21) Appl. No.: 11/749,475

(22) Filed: May 16, 2007

(65) Prior Publication Data

US 2007/0299465 A1 Dec. 27, 2007

Related U.S. Application Data

(60) Provisional application No. 60/805,824, filed on Jun. 26, 2006.

(51) Int. Cl.
*A61F 2/01* (2006.01)
(52) U.S. Cl. .......................................... 606/200
(58) Field of Classification Search .................. 606/200, 606/113, 114, 127, 159
See application file for complete search history.

(56) References Cited

U.S. PATENT DOCUMENTS

| | | | |
|---|---|---|---|
| 4,706,671 A | 11/1987 | Weinrib | |
| 5,375,612 A | 12/1994 | Cottenceau et al. | |
| 5,814,064 A | 9/1998 | Daniel et al. | |
| 5,846,260 A | 12/1998 | Maahs | |
| 5,895,399 A | 4/1999 | Barbut et al. | |
| 5,910,154 A | 6/1999 | Tsugita et al. | |
| 5,911,734 A | 6/1999 | Tsugita et al. | |
| 5,941,896 A | 8/1999 | Kerr | |
| 5,947,995 A | 9/1999 | Samuels | |
| 6,001,118 A | 12/1999 | Daniels et al. | |
| 6,007,557 A | 12/1999 | Ambrisco et al. | |
| 6,027,520 A | 2/2000 | Tsugita et al. | |
| 6,042,598 A | 3/2000 | Tsugita et al. | |
| 6,053,932 A | 4/2000 | Daniels et al. | |
| 6,129,739 A | 10/2000 | Khosravi | |
| 6,152,946 A | 11/2000 | Broome et al. | |
| 6,165,200 A | 12/2000 | Tsugita et al. | |
| 6,179,861 B1 | 1/2001 | Khosravi et al. | |
| 6,235,044 B1 | 5/2001 | Root et al. | |
| 6,245,087 B1 * | 6/2001 | Addis | 606/200 |
| 6,245,089 B1 | 6/2001 | Daniel et al. | |
| 6,371,969 B1 | 4/2002 | Tsugita et al. | |
| 6,391,044 B1 | 5/2002 | Yadav et al. | |
| 6,425,909 B1 | 7/2002 | Dieck et al. | |
| 6,506,205 B2 | 1/2003 | Goldberg et al. | |
| 6,508,826 B2 | 1/2003 | Murphy et al. | |
| 6,520,978 B1 | 2/2003 | Blackledge et al. | |
| 6,540,768 B1 | 4/2003 | Diaz et al. | |
| 6,544,279 B1 | 4/2003 | Hopkins et al. | |

(Continued)

FOREIGN PATENT DOCUMENTS

EP 1 479 357 A1 11/2004
(Continued)

*Primary Examiner* — Katherine Dowe
(74) *Attorney, Agent, or Firm* — Seager, Tufte & Wickhem LLC

(57) ABSTRACT

A distal protection device that may include a guidewire having a proximal end and a distal end, a filter disposed on the guidewire, the filter including filtering material and an expandable hollow coil, and a wire at least partially disposed within the coil, wherein the filter is actuatable from a closed position to an open position by reducing tension on the wire and methods of use thereof.

24 Claims, 6 Drawing Sheets

U.S. PATENT DOCUMENTS

| | | | |
|---|---|---|---|
| 6,562,058 B2 | 5/2003 | Seguin et al. | |
| 6,592,546 B1 | 7/2003 | Barbut et al. | |
| 6,610,077 B1 | 8/2003 | Hancock et al. | |
| 6,616,680 B1 | 9/2003 | Thielen | |
| 6,663,650 B2 | 12/2003 | Sepetka et al. | |
| 6,663,651 B2 | 12/2003 | Krolik et al. | |
| 6,676,682 B1 | 1/2004 | Tsugita et al. | |
| 6,726,703 B2 * | 4/2004 | Broome et al. | 606/200 |
| 6,740,061 B1 * | 5/2004 | Oslund et al. | 604/104 |
| 6,790,219 B1 | 9/2004 | Murphy | |
| 6,805,699 B2 | 10/2004 | Shimm | |
| 6,936,059 B2 | 8/2005 | Belef | |
| 6,964,673 B2 | 11/2005 | Tsugita et al. | |
| 6,974,469 B2 | 12/2005 | Broome et al. | |
| 7,094,249 B1 | 8/2006 | Broome et al. | |
| 7,125,414 B2 | 10/2006 | Blackledge et al. | |
| 7,192,434 B2 | 3/2007 | Anderson et al. | |
| 7,261,727 B2 | 8/2007 | Thielen | |
| 7,326,226 B2 | 2/2008 | Root et al. | |
| 7,410,491 B2 | 8/2008 | Hopkins et al. | |
| 2003/0100919 A1 * | 5/2003 | Hopkins et al. | 606/200 |
| 2005/0119691 A1 * | 6/2005 | Daniel et al. | 606/200 |
| 2005/0131449 A1 * | 6/2005 | Salahieh et al. | 606/200 |
| 2005/0251201 A1 * | 11/2005 | Roue et al. | 606/213 |
| 2006/0015136 A1 * | 1/2006 | Besselink | 606/200 |
| 2006/0212068 A1 * | 9/2006 | Boylan et al. | 606/200 |
| 2008/0275485 A1 * | 11/2008 | Bonnette et al. | 606/200 |

FOREIGN PATENT DOCUMENTS

| | | |
|---|---|---|
| WO | 98/38920 A1 | 9/1998 |
| WO | 99/55236 A1 | 11/1999 |
| WO | 03/075997 A1 | 9/2003 |

* cited by examiner

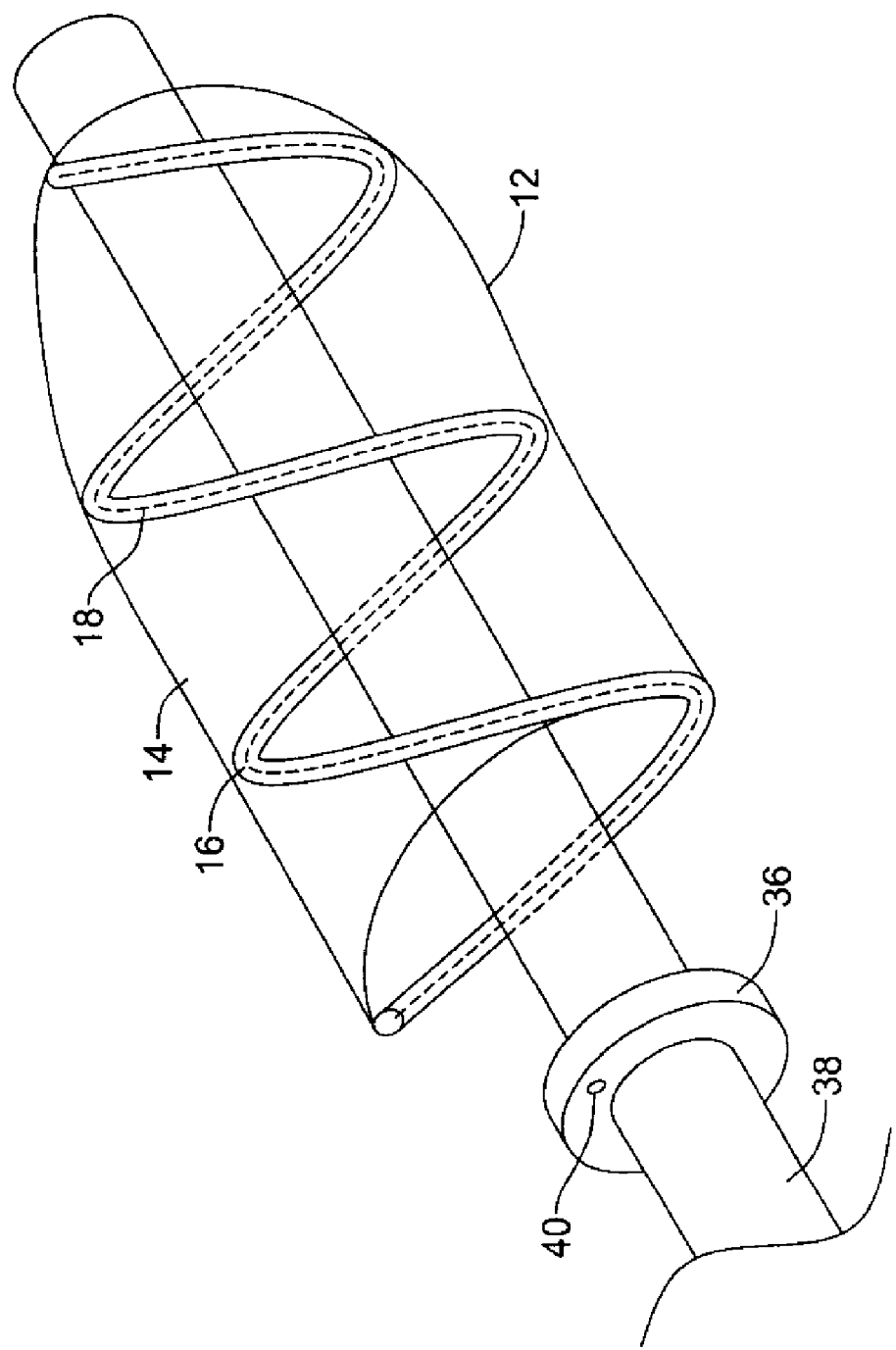

SELF-OPENING FILTER WITH WIRE ACTUATION

This application claims the benefit of U.S. Provisional Application No. 60/805,824, entitled "SELF-OPENING FILTER WITH WIRE ACTUATION," filed Jun. 26, 2006, the entirety of which is herein incorporated by reference.

FIELD

The invention pertains to the field of percutaneous filters such as intravascular filters and more particularly to expandable or actuatable percutaneous filters and methods of use thereof.

BACKGROUND

Heart disease is a major problem in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire such that the balloon is positioned adjacent a stenotic lesion. The balloon is then inflated and the restriction of the vessel is opened. During an atherectomy procedure, the stenotic lesion may be mechanically cut away from the blood vessel wall using an atherectomy catheter.

During angioplasty and atherectomy procedures, embolic debris can be separated from the wall of the blood vessel. If this debris enters the circulatory system, it could block other vascular regions including the neural and pulmonary vasculature, both of which are highly undesirable. During angioplasty procedures, stenotic debris may also break loose due to manipulation of the blood vessel. Because of this debris, a number of devices, termed distal protection devices, have been developed to filter out this debris. There is an ongoing need for new and improved distal protection devices.

SUMMARY

One embodiment pertains to a distal protection device that includes a guidewire having a proximal end and a distal end, a filter disposed on the guidewire, the filter including filtering material and an expandable hollow coil, and a wire at least partially disposed within the coil, wherein the filter is actuatable from a closed position to an open position by reducing tension on the wire. The coil includes a plurality of loops and wherein the loops are spaced apart in the open position of the filter and spaced closer together in the closed position and the loops may abut in the closed position. The filtering material may define a proximally facing cavity having a mouth where the coil is attached to the mouth. Alternatively the coil may spiral along a portion of the length of the filtering material where the coil has a proximal end attached to the filtering material proximal end and a distal end attached to the guidewire. In another embodiment, the coil may have a helical shape and have a proximal end attached to the filtering material proximal end and a distal end attached to the guidewire proximate the filtering material distal end. The coil loops may be made form a nickel-titanium alloy such as nitinol or another suitable alloy such as a superelastic alloy or a spring steel alloy and may have a circular cross-section or a rectangular cross-section. One end of the coil may be fixed to the guidewire and one end may be fixed only to the filtering material or both ends of the coil may be fixed to the guidewire. The device may include a slider tube disposed on the guidewire to which the filter is attached, a stop disposed proximal of the slider tube and a stop distal the slider tube. The guidewire may be solid or hollow or have a solid portion and an hollow portion such as a solid distal portion of approximately 120 centimeters in length and a hollow proximal portion. For those embodiments where the guidewire has a hollow portion, the guidewire may include an opening from the guidewire lumen proximal the filter where the wire is threadably disposed through the opening and into the guidewire lumen. The wire may include a weakness such as a knot, a neck or a perforation. If the weakness is a knot the guidewire may define an opening distal a lumen in which the wire is partially disposed, and where the opening is just proximal the knot and smaller than the knot; the guidewire may include a collar in which the opening is defined. The wire may be a polymeric member, a metallic member or other suitable member. The wire may be a component having high tensile strength and low columnar strength such as a fiber or a string. For example the wire may be a Kevlar string.

One embodiment pertains to a method of use in which the steps may include providing a filter disposed on a guidewire, the filter having filtering material attached to a hollow coil, providing a wire in tension disposed partially in the coil, the wire tension keeping the coil in a compacted configuration, and releasing the tension in the wire to allow the coil to expand to an open configuration and thereby open the filter. The step of releasing the tension in the wire may include the step of moving the wire distally relative to the guidewire or, where the wire comprises a distal section connected by a weakness to a proximal section, the step of releasing the tension may include the step of separating the proximal portion from the distal portion. Where the weakness is a knot, this step may include forcing a knot in the wire against a surface of the guidewire until the wire separates. This step may alternatively include the step of releasing the tension includes the step of pulling the wire proximally.

Another embodiment pertains to a distal protection device that may include an elongate member having a proximal end and a distal end, a filter disposed on the elongate member, the filter including a filtering material connected to a hollow expandable coil, the filter actuatable between a collapsed configuration and an expanded configuration, the coil having a first end and a second end and defining a lumen therebetween, and a wire threaded through the lumen of the coil, the wire being attached to the first end and extending out from the second end. The coil includes a plurality of loops that are spaced apart when the filter is in the expanded configuration and spaced more closely together when the filter is in the collapsed configuration, which loops may abut when the filter is in the collapsed configuration. The filter is actuatable between the expanded configuration and the collapsed configuration by the application of tension to the wire. For example the filter may be moved from the expanded configuration to the collapsed configuration by pulling the wire proximally.

BRIEF DESCRIPTION OF THE DRAWINGS

The invention may be more completely understood in consideration of the following detailed description of various embodiments of the invention in connection with the accompanying drawings in which.

FIG. 4 is an orthogonal diagrammatic view of the distal portion of the embodiment of FIG. 3 in a second configuration.

DETAILED DESCRIPTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

Figure 1A:
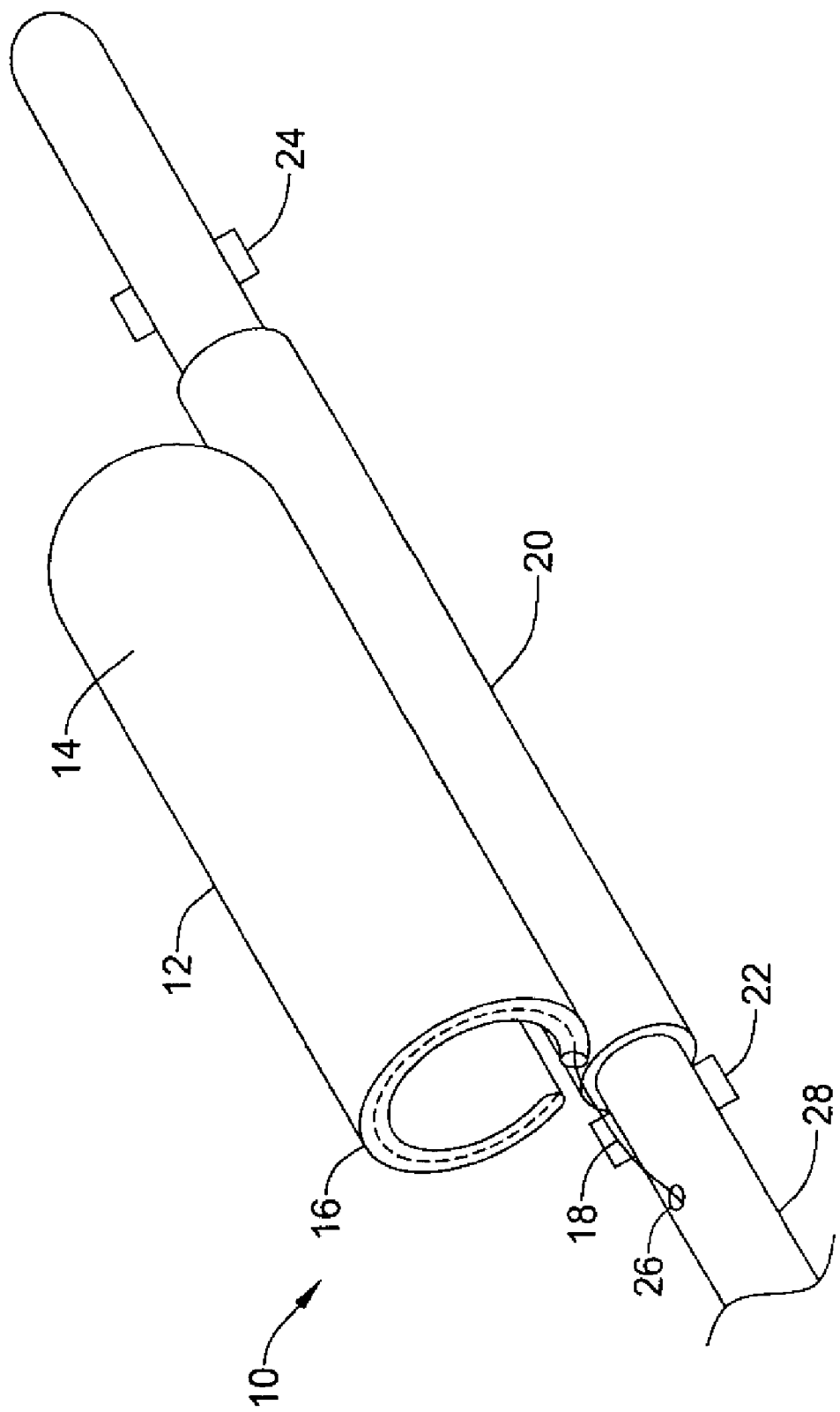
FIG. 1A is an orthogonal diagrammatic view of the distal portion of an embodiment in a first configuration.
Figure 1B:
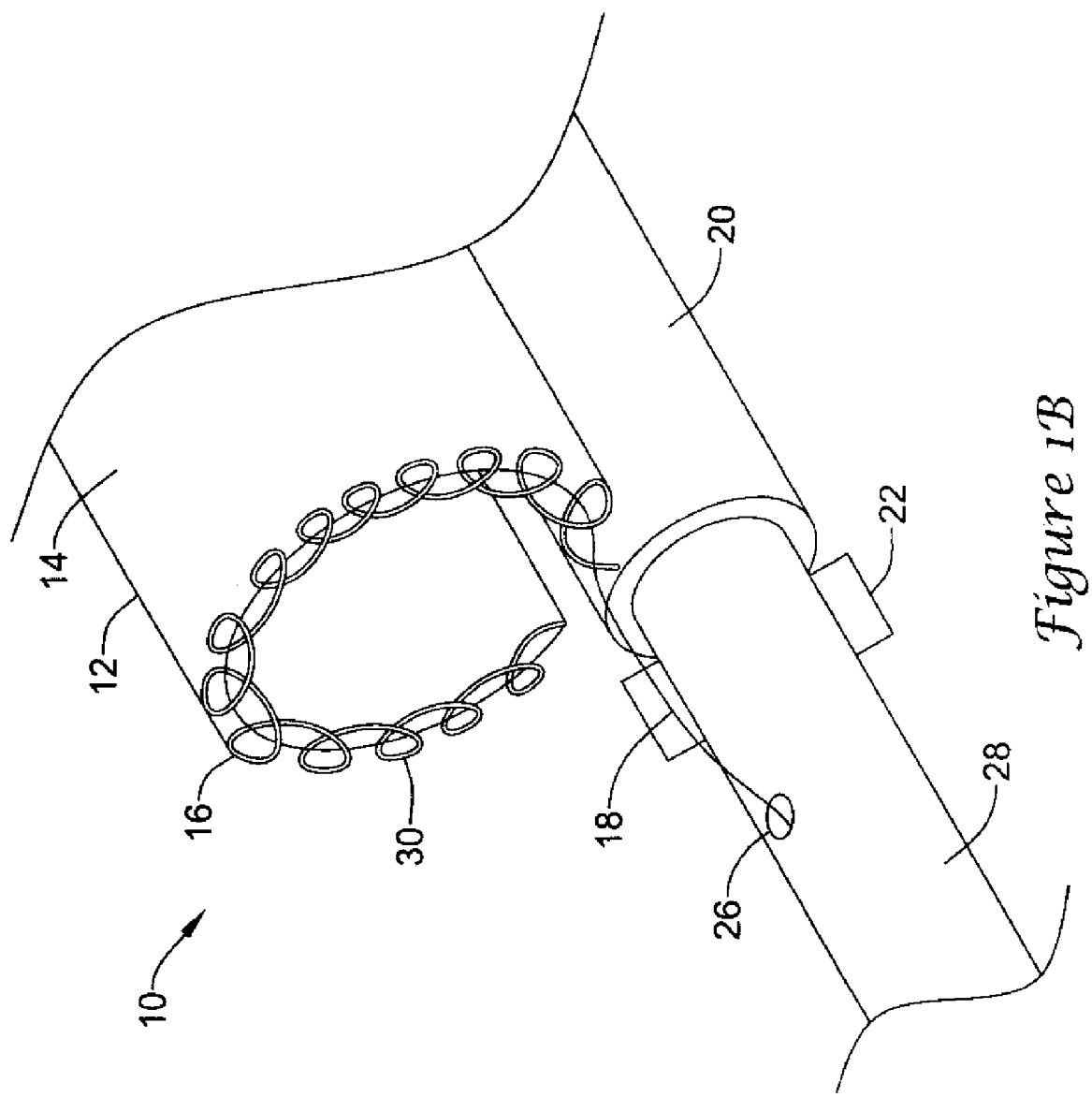
FIG. 1B is an orthogonal diagrammatic partial view of the embodiment of claim 1 in the first configuration.

Referring now to FIG. 1A, which is an orthogonal diagrammatic view of the distal portion of a distal protection device 10, a filter 12 disposed on a guide wire 28 is shown. Filter 12 includes a ring-shaped coil 16 which is biased into this open, expanded shape and which holds open the proximal mouth of filtering material 14. Coil 16 is mounted on spinner tube 20 which is slidably disposed on guide wire 28 and prevented from sliding proximally by stop 22 and which may be optionally prevented from sliding distally by stop 24. A wire 18 is threaded through guide wire 28, which is hollow and through coil 16, which is hollow as well, and is attached to the end of coil 16. FIG. 1B, which is an orthogonal diagrammatic view of a portion of distal protection device 10, illustrates coil 16 in greater detail. Coil 16 comprises several loops 30 that are spaced apart from each other and to which filtering material 14 is attached.

Figure 2A:
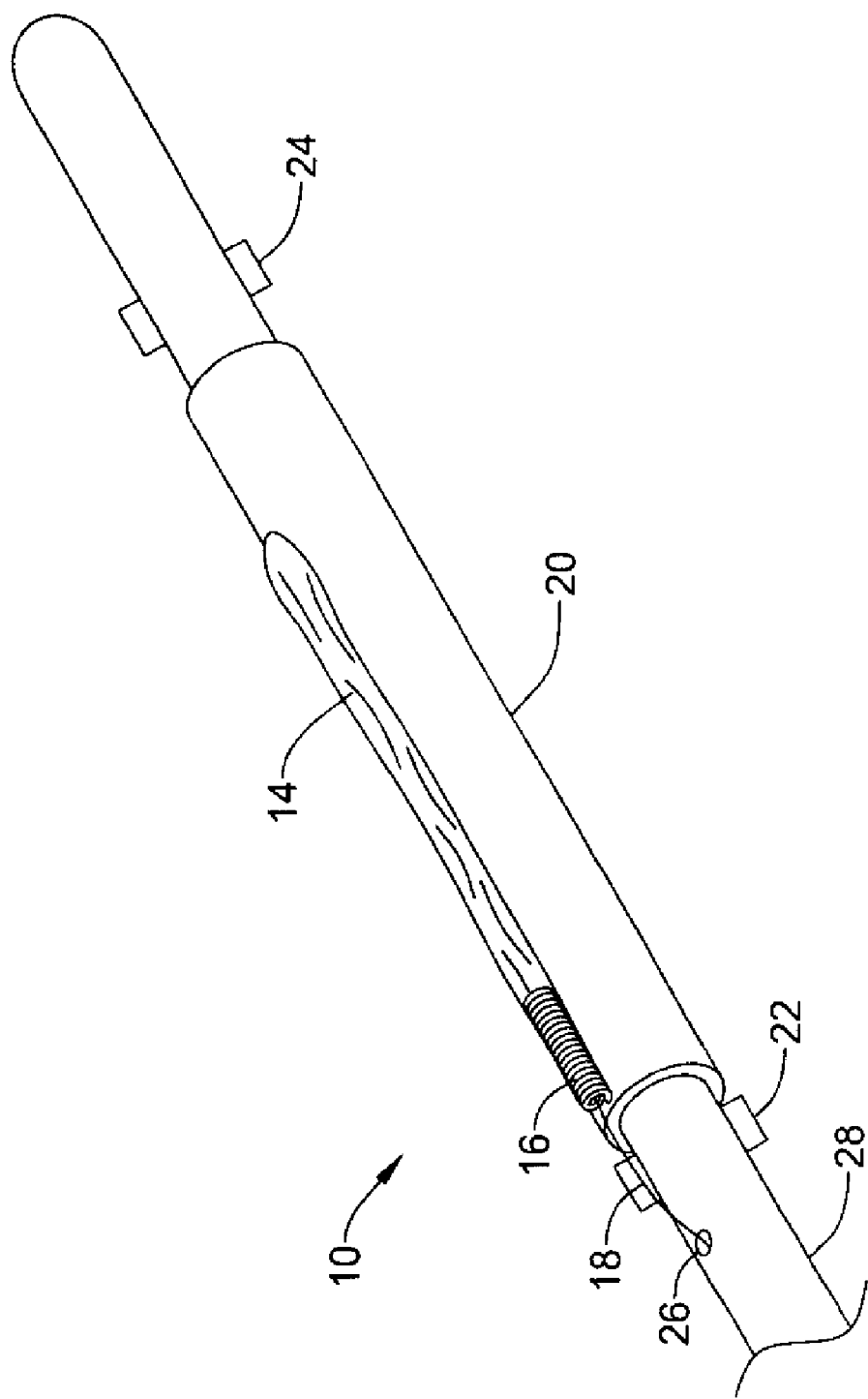
FIG. 2A is an orthogonal diagrammatic view of the distal portion of an embodiment of claim 1 in a second configuration.
Figure 2B:
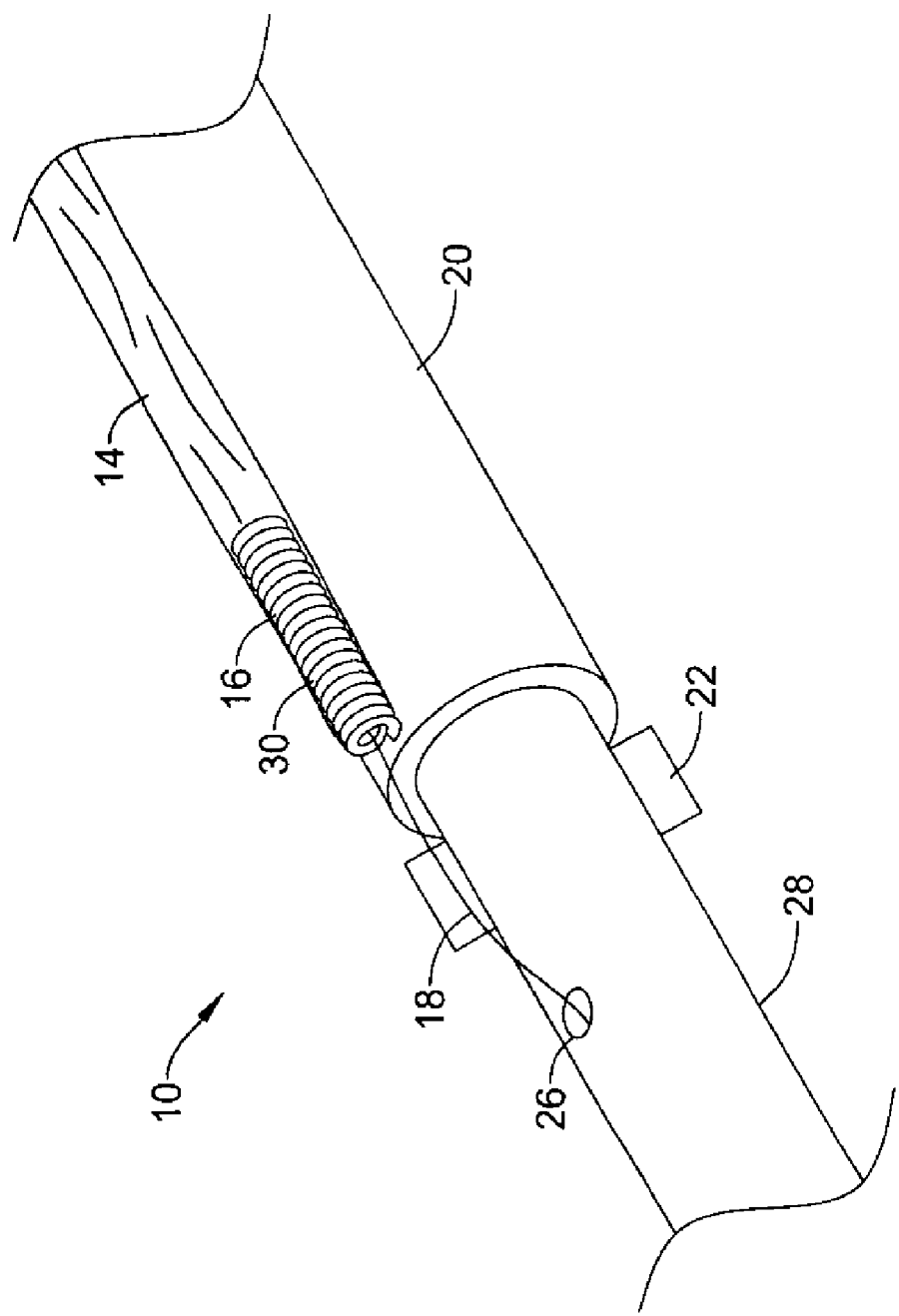
FIG. 2B is an orthogonal diagrammatic partial view of a portion of the embodiment of claim 1 in the second configuration.

The filter may be actuated to the closed position by moving wire 18 proximally relative to the filter. When wire 18 is pulled, coil 16 may be collapsed flat against spinner tube 20 as is shown in FIG. 2A, which is an orthogonal diagrammatic view of the distal portion of distal protection device 10. As may be more easily seen in FIG. 2B, the wire 18 collapses the filter by moving the loops 30 of the coil 16 closer together. If the tension on wire 18 is removed, the coil 16 will expand back to the shape depicted in FIG. 1A.

Figure 3:
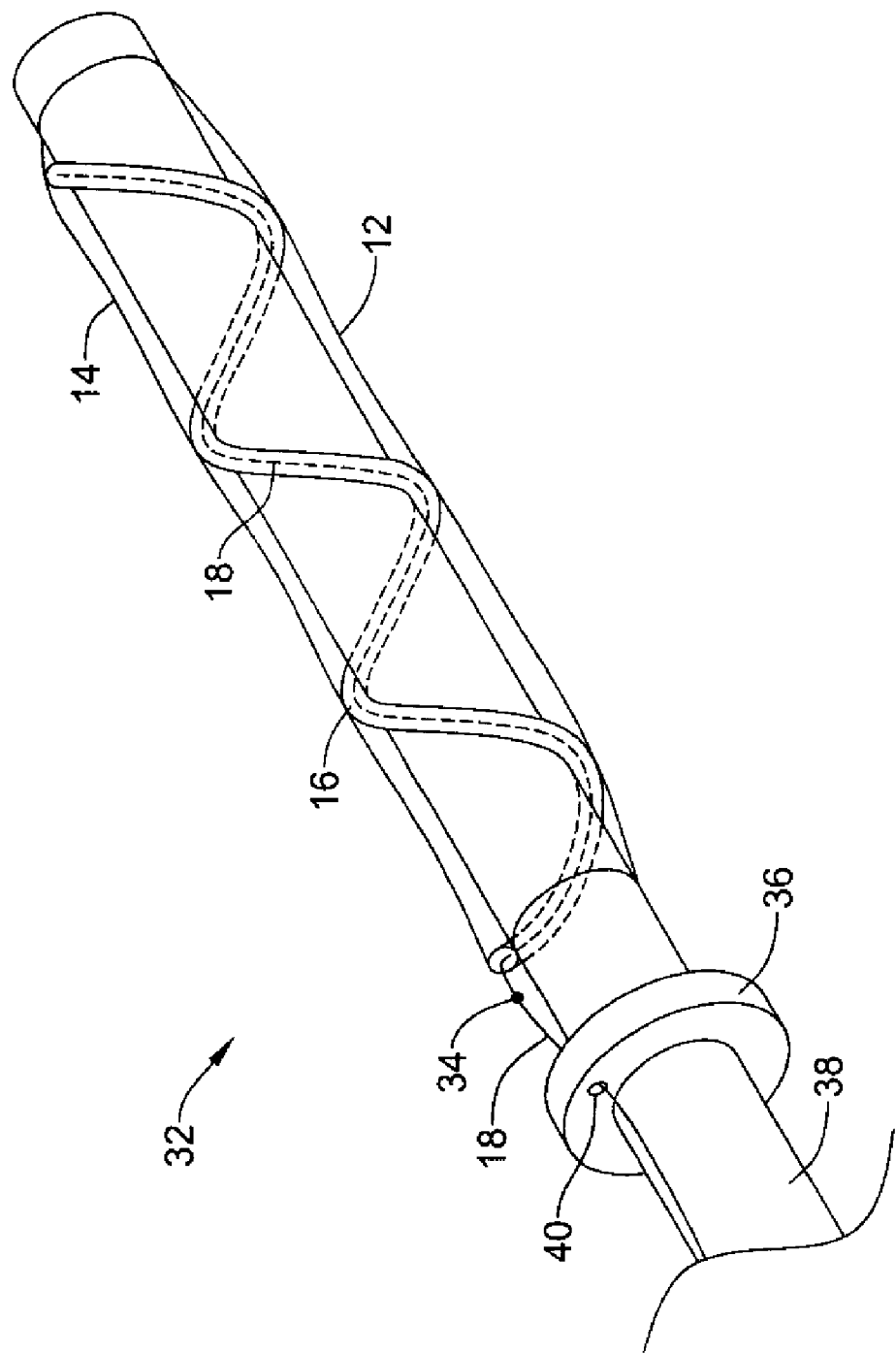
FIG. 3 is an orthogonal diagrammatic view of the distal portion of a second embodiment in a first configuration.

A second embodiment is depicted in FIG. 3, which is an orthogonal diagrammatic view of a distal protection device 32. A filter 12 is made of a filtering material 14 attached at its distal end to guide wire 38 and a coil 16 that is disposed within filtering material 14 and attached at its proximal end to the filtering material and at its distal end to the guide wire. A wire 18 is threaded through coil 16 and tension on the wire keeps coil 16 against guidewire 38. Coil 16 is similar to that of the previous embodiments and is made of loops (not pictured) kept by the operation of the wire close against the guide wire 38. The wire 18 may have a knot 34 and may be threaded through an opening 40 in a collar 36, where the knot cannot pass through the opening. This distal protection device may be actuated by pulling on wire 18, forcing knot 34 against collar 36 and breaking the wire at that point. All tension being thereby removed from the distal portion of the wire, coil 16 expands, expanding filter 12 to its open position as shown in FIG. 4, where the loops of the coil are expanded from each other. Knot 34 may be a perforation or neck or other weakness in the wire. In some embodiments, collar 40 is not necessary. In some embodiments, there is no weakness such as knot 34 and the filter is expanded by releasing wire 18 as in the previous embodiment. Wire 18 need extend all the way through coil 16 which can be self expanding.

These two embodiments illustrate the invention generally, but the invention is by no means limited to that discussed above. The guidewire may be a hollow hypotube or a solid shaft and in the first instance the wire may or may not be threaded through the guidewire. In one embodiment, the guide wire may have a solid proximal portion and a hollow distal portion. The wire may in this embodiment be threaded through the hollow distal portion. The wire may be any material having suitable flexibility and tensile strength. It may be, for instance, a polymer string such as a Kevlar fiber. The filtering material may be any suitable filtering material; it may be a mesh or weave made from nitinol or polymer threads; it may be a polymer sheet having holes cut or drilled therein to provide a means of filtering particles of a desired size from the blood stream. The coil may be made from superelastic nitinol or other suitable alloy capable of suitable deformation. Some spring steels may be suitable, for instance. The wire used in the coil may have a circular cross-section, a rectangular cross section or other suitable cross-section. The stops may be metal or polymeric bumps welded to or adhered to the guidewire.

Distal protection devices having coils of varying configurations are contemplated. For instance, in the device of FIG. 1, both ends of the coil may be attached to the slider tube; in this case when the coil is collapsed by the operation of the wire the loops would form two rows. In another example variation, the coil and the filtering material could be configured to envelope the slider tube with both ends of the coil attached to the slider tube; in this case the coil would form a smaller coil in contact with the surface of the slider tube when collapsed.

The embodiments of this invention may be used with other devices. For example, the device may be delivered to the area of interest in a delivery sheath and collected by a retrieval sheath. Other therapy catheters such as stent delivery catheters and angioplasty catheters may be delivered over the device. Further, other components such as radiopaque bands and atraumatic distal tips may be used with embodiments of this invention. In short, the embodiments of this invention are distal protection devices and may be used with components and other devices typically used with such devices.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. None of the description in the present application should be read as implying that any particular element, step, or function is an essential element which must be included in the claim scope. Moreover, none of these claims are intended to invoke 35 U.S.C. §112, ¶6 unless the exact words "means for" are followed by a participle. The invention's scope is, of course, defined in the language in which the appended claims are expressed.

What is claimed is:

1. A distal protection device comprising:
   a guidewire having a proximal end and a distal end;

a filter disposed on the guidewire, the filter including filtering material and an expandable hollow coil; wherein the filtering material defines a proximally facing cavity having a mouth and wherein the coil circumscribes the mouth; and a wire attached to a distal end of the coil and at least partially disposed within the coil;

wherein the filter is actuatable from a closed position to an open position by reducing tension on the wire.

2. The device of claim 1 wherein the coil comprises a plurality of loops and wherein the loops are spaced apart in the open position of the filter and spaced closer together in the closed position.

3. The device of claim 2 wherein the loops abut in the closed position.

4. The device of claim 2 wherein the loops are made from nitinol.

5. The device of claim 2 wherein the loops comprise wire having a circular cross-section.

6. The device of claim 2 wherein the loops comprise wire having a rectangular cross-section.

7. The device of claim 1 wherein the coil has a first end that is fixed.

8. The device of claim 7 wherein the coil has a second end that is fixed.

9. The device of claim 7 wherein the coil has a second end attached only to the filtering material.

10. The device of claim 1 further comprising
a slider tube disposed on the guidewire;
a stop disposed proximal of the slider tube; and
wherein the filter is attached to the slider tube.

11. The device of claim 1 wherein the guidewire comprises a hollow portion having a lumen.

12. The device of claim 11 wherein the guidewire comprises an opening from the guidewire lumen proximal the filter and wherein the wire is at least partially disposed in the lumen.

13. The device of claim 11 wherein the guidewire comprises a solid portion proximal the hollow portion.

14. The device of claim 13 wherein the solid portion is between 100 and 140 centimeters in length.

15. The device of claim 1 wherein the wire is a polymeric member.

16. The device of claim 1 wherein the wire is a component that has high tensile strength and low columnar strength.

17. The device of claim 1 wherein the wire is Kevlar string.

18. A method of opening a distal protection filter comprising the steps of
providing a filter disposed on a guidewire, the filter having filtering material attached to a hollow coil; wherein filtering material defines a proximally facing cavity having a mouth and wherein the coil circumscribes the mouth;
providing a wire in tension attached to a distal end of the coil and disposed partially in the coil, the wire tension keeping the coil in a compacted configuration; and
releasing the tension in the wire to allow the coil to expand to an open configuration and thereby open the filter.

19. The method of claim 18 wherein the step of releasing the tension in the wire comprises the step of moving the wire distally relative to the guidewire.

20. A distal protection device comprising
an elongate member having a proximal end and a distal end;
a filter disposed on the elongate member, the filter including a filtering material connected to a hollow expandable wherein the filtering material defines a proximally facing cavity having a mouth and wherein the coil circumscribes the mouth; and, the coil having a first end and a second end and defining a lumen therebetween; and
a wire threaded through the lumen of the coil, the wire being attached to the first end and extending out from the second end; and wherein the filter is actuatable from a collapsed configuration to an expanded configuration by reducing tension on the wire.

21. The device of claim 20 wherein the coil comprises a plurality of loops that are spaced apart when the filter is in the expanded configuration and spaced more closely together when the filter is in the collapsed configuration.

22. The device of claim 21 wherein the loops abut when the filter is in the collapsed configuration.

23. The device of claim 20 wherein the filter is actuatable between the expanded configuration and the collapsed configuration by the application of tension to the wire.

24. The device of claim 20 wherein the filter is moved from the expanded configuration to the collapsed configuration by pulling the wire proximally.

\* \* \* \* \*